(12) United States Patent  
Jensen et al.

(10) Patent No.: US 7,677,799 B2  
(45) Date of Patent: Mar. 16, 2010

(54) COORDINATION OF RADIOLOGICAL IMAGING SUBSYSTEMS AND COMPONENTS

(75) Inventors: Vernon Thomas Jensen, Draper, UT (US); Francois Emmanuel Falco, South Jordan, UT (US); David Ellis Barker, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 65 days.

(21) Appl. No.: 11/495,865

(22) Filed: Jul. 28, 2006

(65) Prior Publication Data

US 2008/0025471 A1 Jan. 31, 2008

(51) Int. Cl.  
*G01D 18/00* (2006.01)

(52) U.S. Cl. .................... 378/205; 378/195

(58) Field of Classification Search .......... 378/102, 378/198, 197, 205, 195, 117, 207  
See application file for complete search history.

(56) References Cited

U.S. PATENT DOCUMENTS 6,999,558 B2 * 2/2006 Okoda .................... 378/102

2002/0188194 A1 * 12/2002 Cosman .................. 600/426  
2005/0281378 A1 * 12/2005 Schmitt .................. 378/117

* cited by examiner

*Primary Examiner*—Hoon Song  
(74) *Attorney, Agent, or Firm*—McAndrews, Held & Malloy, Ltd.; Peter J. Vogel; Michael A. Dellapenna

(57) ABSTRACT

Certain embodiments of the present invention provide a system for coordinating a radiological imaging subsystem with a component including: a first communication device located on the radiological imaging subsystem; and a second communication device located on the component, wherein the first and second communication devices are capable of communicating to indicate a positional relationship between the radiological imaging subsystem and the component. In an embodiment, the component includes an imaging table. In an embodiment, at least one range of motion of the radiological imaging system is determinable based at least in part on the communicating to indicate a positional relationship. In an embodiment, the at least one range of motion of the radiological imaging system includes at least one range of motion of a gantry.

26 Claims, 4 Drawing Sheets

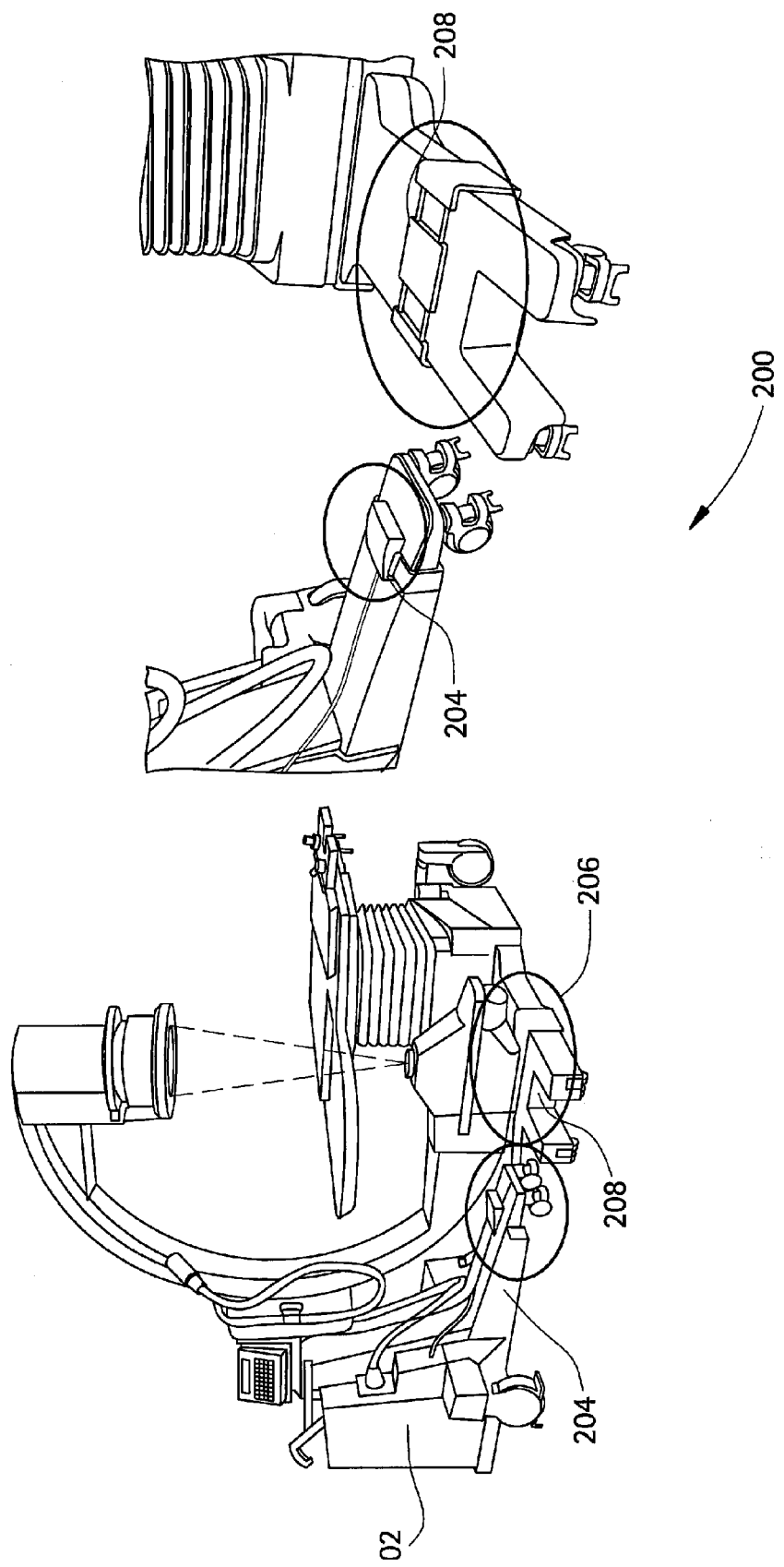

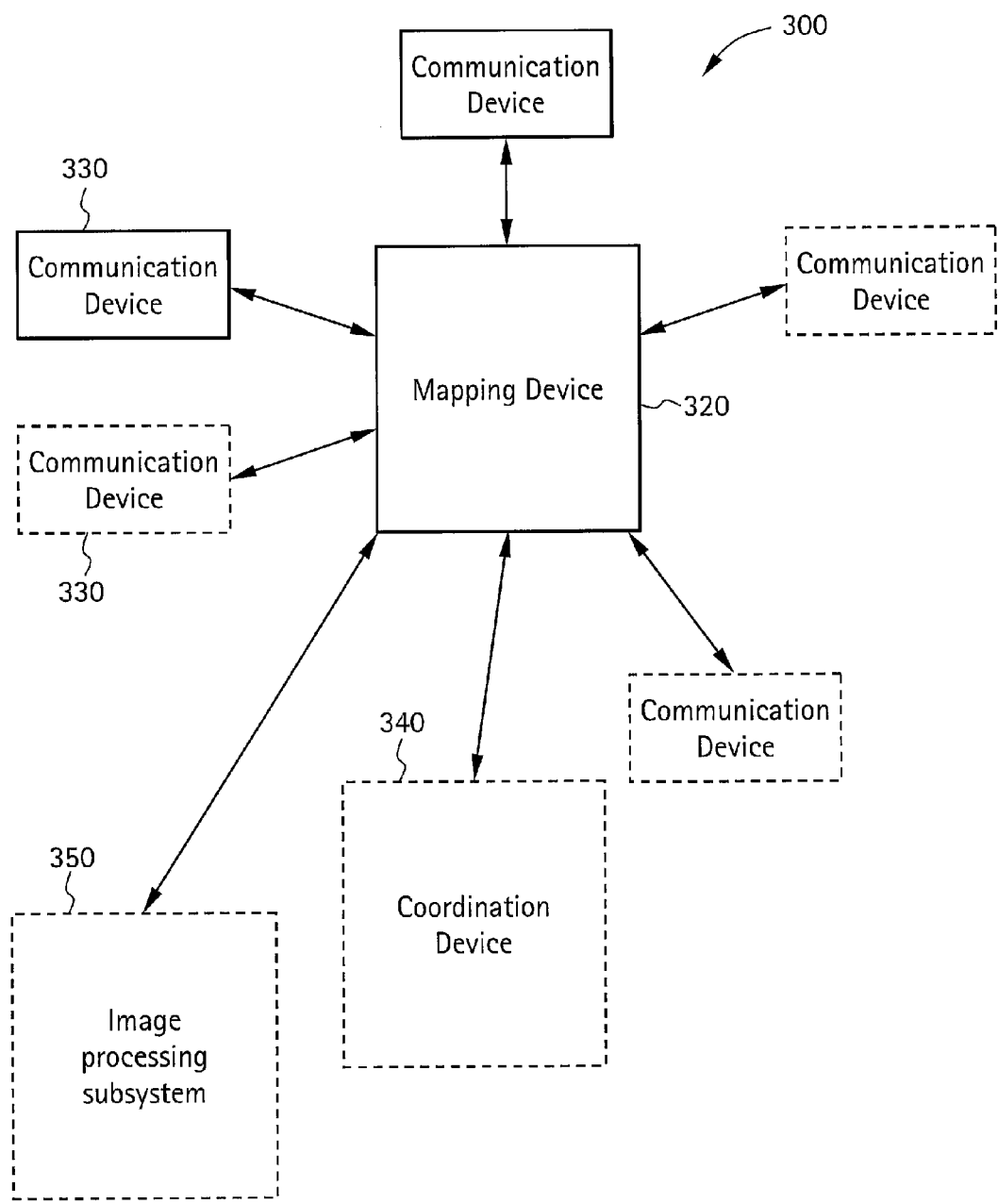

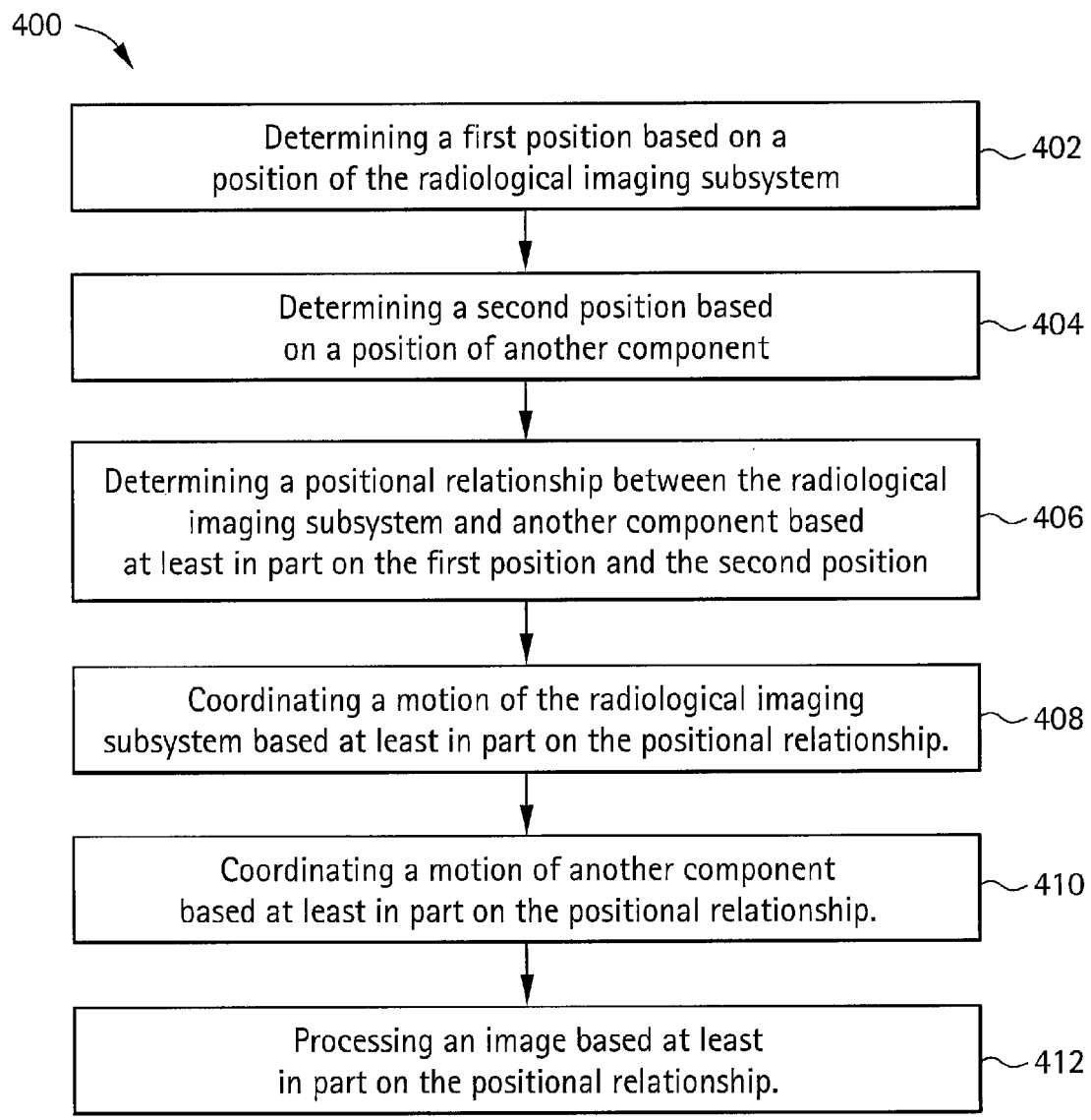

COORDINATION OF RADIOLOGICAL IMAGING SUBSYSTEMS AND COMPONENTS

BACKGROUND OF THE INVENTION

Embodiments of the present application relate generally to registering two or more data sets, generally for use in clinical applications. Particularly, certain embodiments relate to identifying differences between an output from an imaging subsystem with that of a tracking subsystem automatically.

Mobile C-arms may be common imaging apparatus used today in surgery. Some advantages of mobile C-arms may include versatility, mobility, and economy than as compared to fixed-room x-ray systems. Technology advances in several key areas (e.g. image processing, CPU speeds, digital data storage capacities, miniaturization, motorization) have, in part, fueled the increasing popularity of mobile C-arm systems as compared to the popularity of fixed-room systems.

One advantage of fixed-room systems may be in the area of gantry automation. Since fixed-room systems may typically be structurally integrated into a room, fixed-room systems do not have the same design constraints of a mobile system when it comes to electrical power, size, weight, etc. Thus, structural integration in fixed-room systems to have relatively fast and sophisticated gantry motion features.

Fixed-room imaging systems may also incorporate the patient table into the overall system gantry design. Knowledge of the position and orientation of the table relative to position and orientation of the imaging gantry, enables more advanced positioning and imaging functions, such as collision avoidance and high-speed gantry motion. Mobile systems may be limited in this area because the patient table may not be integrated into the overall system gantry design.

However, even fixed-room imaging systems may not be able to obtain a full range of motion (e.g. motion of the gantry, and motion of the imaging table). Without real-time positional information of the various sub-components, it may not be possible to obtain a full range of synchronized motion from the movable components.

Thus, there is a need for radiological imaging subsystems capable of performing advanced gantry functions and collision avoidance. There is a need for radiological imaging systems to coordinate motion between an imaging table and a radiological imaging subsystem. Additionally, there is a need for radiological imaging methods and systems that can ascertain the position and/or orientation of other components.

BRIEF SUMMARY OF THE INVENTION

Certain embodiments of the present invention provide a system for coordinating a radiological imaging subsystem with a component including: a first communication device located on the radiological imaging subsystem; and a second communication device located on the component, wherein the first and second communication devices are capable of communicating to indicate a positional relationship between the radiological imaging subsystem and the component. In an embodiment, the component includes an imaging table. In an embodiment, at least one range of motion of the radiological imaging system is determinable based at least in part on the communicating to indicate a positional relationship. In an embodiment, the at least one range of motion of the radiological imaging system includes at least one range of motion of a gantry. In an embodiment, the first and second communication devices are capable of communicating in a medium including at least one of: an active radio frequency medium, an active optical medium, an active sonic medium, a passive radio frequency medium, and a passive optical medium. In an embodiment, the first and second communications devices are capable of communicating with each other. In an embodiment, the first and second communication devices are capable of communicating with a third device to indicate a positional relationship between the radiological imaging subsystem and the component. In an embodiment, the radiological imaging subsystem includes a mobile radiological imaging subsystem. In an embodiment, the system further includes an image processing subsystem capable of receiving the positional relationship to process radiological image information generated by the radiological imaging subsystem.

Certain embodiments of the present invention provide a method for coordinating a radiological imaging subsystem with a component including: determining a first position based on a position of the radiological imaging subsystem; determining a second position based on a position of the proximal component; determining a positional relationship between the radiological imaging subsystem and the component based at least in part on the first position and the second position; and coordinating a motion of the radiological imaging subsystem based at least in part on the positional relationship. In an embodiment, the method further includes coordinating a motion of the component based on the positional relationship. In an embodiment, the determining the first position includes communicating with a first device located on the radiological imaging subsystem to obtain the first position. In an embodiment, the determining the second position includes communicating with a second device located on the component. In an embodiment, the method further includes communicating between a first device located on the radiological imaging subsystem and a second device located on the proximal component to determine the first and second positions. In an embodiment, the motion of the radiological imaging subsystem includes a motion of a gantry. In an embodiment, the proximal component includes an imaging table. In an embodiment, the method further includes processing an image based at least in part on the positional relationship.

Certain embodiments of the present invention provide a computer-readable storage medium including a set of instructions for a computer, the set of instructions including: a reception routine for receiving positional information provided by a first communication device and a second communication device; a determination routine for determining a positional relationship of a radiological imaging subsystem and a component, the positional relationship based at least in part on the positional information; and a coordination routine for coordinating a motion of the radiological imaging subsystem with respect to a position of the component. In an embodiment, the set of instructions further includes a coordination routine for coordinating a motion of the component with respect to a position of the radiological imaging system. In an embodiment, the first communication device is located on the radiological imaging subsystem. In an embodiment, the second communication device is located on the component. In an embodiment, the first and second communication devices are capable of communicating with each other. In an embodiment, the set of instructions further includes an image processing routine capable of receiving the positional information for processing image information from the radiological imaging subsystem.

Certain embodiments of the present invention provide a system for coordinating a radiological imaging subsystem with a component including: a first communication device located on the radiological imaging subsystem, the first communication device capable of communicating information corresponding to a position of the radiological imaging subsystem; a second communication device located on the component, the second communication device capable of communicating information corresponding to a position of the component; and a mapping device capable of receiving the information corresponding to the position of the radiological imaging subsystem and the position of the component to determine a spatial relationship between the radiological imaging subsystem and the component. In an embodiment, the system further includes a coordination device for coordinating a motion of the radiological imaging subsystem with respect to the component based at least in part on the spatial relationship. In an embodiment, the system further includes a coordination device for coordinating a motion of the component with respect to the radiological imaging subsystem based at least in part on the spatial relationship. In an embodiment, the radiological imaging subsystem is substantially mobile. In an embodiment, the first and second communication devices are capable of communicating with each other. In an embodiment, the system further includes an image processing subsystem capable of receiving the spatial relationship for processing image information from the radiological imaging subsystem.

BRIEF DESCRIPTION OF SEVERAL VIEWS OF THE DRAWINGS

FIG. 2 shows a system for coordinating a radiological imaging subsystem with a component, according to an embodiment of the present invention.

FIG. 3 shows a system for coordinating a radiological imaging subsystem with a component, according to an embodiment of the present invention.

FIG. 4 shows a flow chart for a method for coordinating a radiological imaging subsystem with a component, according to an embodiment of the present invention.

Figure 1:
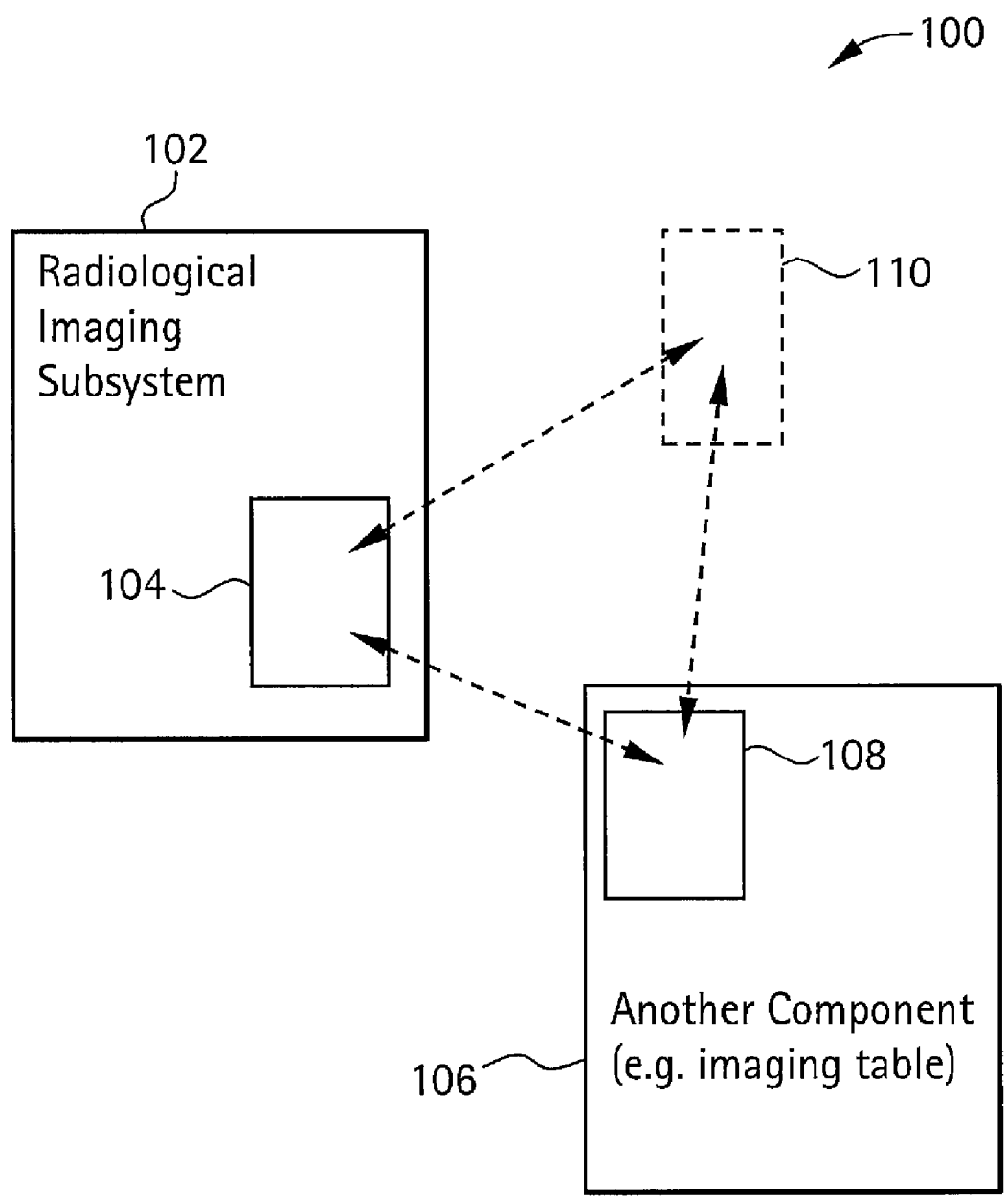
FIG. 1 shows a system for coordinating a radiological imaging subsystem with a component, according to an embodiment of the present invention.

The foregoing summary, as well as the following detailed description of certain embodiments of the present application, will be better understood when read in conjunction with the appended drawings. For the purpose of illustrating the invention, certain embodiments are shown in the drawings. It should be understood, however, that the present invention is not limited to the arrangements and instrumentality shown in the attached drawings. Further, some figures may be representations of the type of display and/or output associated with methods and systems of the present invention, in accordance with one or more embodiments.

DETAILED DESCRIPTION OF THE INVENTION

FIG. 1 shows a system 100 for coordinating a radiological imaging subsystem with a component, according to an embodiment of the present invention. System 100 may include a radiological imaging subsystem 102, a first communications device 104, a component 106, and a second communications device 108. In some scenarios, system 100 may also include a third communications device 110.

A radiological imaging subsystem 102 may be capable of any of a variety of radiological modalities. For example, a radiological imaging subsystem 102 may be capable of x-ray, computed tomography, tomosynthesis, ultrasound, positron emission tomography, magnetic resonance imaging, and/or the like. The radiological imaging subsystem 102 may be a fixed system, or may be substantially mobile, for example. A radiological imaging subsystem may include a gantry or a C-Arm, similar to the one shown in FIG. 2, that is a portion of the subsystem 202. A portion of the imaging subsystem 102 may be capable of motion, for example. The gantry, or C-Arm, of the imaging subsystem 102 may be capable of motion, for example. Such motion may occur in one or more dimensions, for example. Some types of motion may be described in Cartesian coordinates (e.g. X, Y, Z, in three dimensions). The motion of a portion of the imaging subsystem 102 may include pitch, roll, and yaw, for example. In the case of a mobile radiological imaging subsystem 102, the entire subsystem 102 may be movable, for example. Fixed radiological imaging subsystems 102 may also be movable, for example. Fixed radiological imaging subsystems 102 may be coarsely moveable (e.g. to a new room), or finely moveable (e.g. small movement to change the orientation of the fixed system, for example.

A component 106 may be any component used in conjunction, or in proximity to, a radiological imaging subsystem 102, for example. For example, the component 106 may be an imaging table, useable in conjunction with a radiological imaging subsystem 102. The component 106 may be substantially fixed, or may be substantially mobile, for example. For example, the component 106 may be a mobile imaging table usable in conjunction with a mobile radiological imaging subsystem. A portion of the component, or the entire component may be movable in one or more directions, for example. An imaging table may be moveable in conjunction with radiological imaging for example.

A first communication device 104 may be located on a radiological imaging subsystem 102, for example. The first communication device 104 may be integrated or may be attachably removable from the radiological imaging subsystem 102. Similarly, a second communication device 108 may be located on the component 106. The second communication device 108 may be integrated or may be attachably removable from the component 106. The communication devices 104, 108 may be wireless or wired, for example. The communications devices 104, 108 may have a processor (such as a CPU, or a microprocessor, a digital signals processor, etc.), a transmitter, and a receiver, for example. The communications devices 104, 108 may be passive devices, such as passive RFID tags, for example. The communications devices 104, 108 may have one or more antennae, for example. The communications devices 104, 108 may contain optics (e.g. lenses, mirrors, lasers) or audio components (e.g. microphones, amplifiers, speakers), for example (e.g. for optical, sonic, or ultrasonic communications). The communications devices 104, 108 may be powered or not powered (e.g. passive RFID tag), for example. The communications devices 104, 108 may be transponders, for example. The communications devices 104, 108 need not be the same, for example. One device may be an active device, and the other a passive transponder, for example.

Both the first and second communication devices 104, 108 may be capable of communicating. The communication devices 104, 108 may be capable of communicating with each other, or may be capable of communicating with another device, such as a third communication device 110, for example. Communications may occur through active or passive communications, for example. A non-inclusive list of possible communications modes includes active electromagnetic communications, active radio frequency communications (e.g. 802.11), passive radio frequency communications (e.g. RFID), active optical communications (e.g. visible, or infrared), passive optical communications (e.g. camera), passive electromagnetic communications, sonic communications (e.g. ultrasonic), and/or the like. For example, a communications mode may be selected to suit an intended clinical environment.

As the devices communicate, it may be possible for one of the devices to track the position of the other devices. For example, it may be possible for the first communication device 104 to track the position of the second communication device 108, or vice versa. As another alternative, it may be possible for a third communication device 110 to track the positions of the first and second devices 104, 108. Thus, information provided through communications between the devices may contain information that corresponds to positional information of the radiological imaging subsystem 102 and/or a component 106. The position of either the radiological imaging subsystem 102 or the component 106 may be a reference position (e.g. X, Y, Z=0). In this situation, it may only be necessary to track the position of the non-referent portion. For example, if the radiological imaging subsystem 102 is chosen to be the reference, then it may only be necessary to track the position of the component 106 with respect to the radiological imaging system 102.

Thus, through communications between devices 104, 108, it may be possible to reveal positional information regarding the relationship between the radiological imaging subsystem 102 and the component 106. There may be additional components, similar to 106 in system 100 (not shown in FIG. 1). Each additional component may have an associated communications device capable of communicating to indicate a positional relationship of the additional component with respect to other components (e.g. component 106) and/or the radiological imaging subsystem 102, for example.

It may also be possible to place a plurality of communication devices on a particular component (e.g. component 106) and/or the radiological imaging subsystem 102. For example, one device may be located on the base of a radiological imaging subsystem 102 to communicate the position of the base. Another device, for example, may be located on the gantry of the radiological imaging subsystem 102 to communicate the position of the gantry.

The positional information provided by communications between the various devices (e.g. 104, 108, 110) may include coordinate position (e.g. Cartesian, polar, etc) and orientation position information. Orientation position may include an angle of inclination (e.g. of an imaging table, or of the gantry), rotation, and/or the like, for example. Positional information may also include a profile of a particular object on which a communications device is located, for example. For example, various radiological imaging subsystems 102 have various profiles (e.g. CT-Scan as compared to Ultrasound). The profile information may be contained in the communication (e.g. a profile code to be used in a look-up table), for example. Profile information may also include a profile of a patient, for example, such as a patient on an imaging table (e.g. a mobile imaging table).

FIG. 2 shows a system 200 for coordinating a radiological imaging subsystem with a component, according to an embodiment of the present invention. System 200 is, in many respects, similar to system 100. A radiological imaging subsystem 202 is shown with a first communication device 204 located (removably attachable) on the base. An imaging table 206 is shown with a second communication device 208 located (removably attachable) on the base. The communication devices 206 and 208 are capable of communications with each other to provide positional information about the radiological imaging subsystem 202 with respect to the imaging table 206. As depicted, both the radiological imaging subsystem 202 and the imaging table 206 are substantially mobile (e.g. having wheels).

FIG. 3 shows a system 300 for coordinating a radiological imaging subsystem with a component, according to an embodiment of the present invention. A mapping device 320 may be capable of receiving positional information from two or more communication devices 330. The mapping device 320 may be capable of direct communications with the communication devices 330, for example, as shown in FIG. 1 with the third communication device 110. Communication may be active, passive, or a combination thereof, for example. Communication may be bi-directional (as shown), or one-way, for example. Alternatively, the mapping device 320 may receive position information of more than one communication device 320 by communicating with a single device. Other communication topologies are also possible (e.g. daisy chain, hub and spoke, hybrid, etc.). A mapping device 320 may be integrated into a communication device 330, or any other various components (e.g. radiological imaging subsystem). A mapping device 320 may also be physically, logically, or conceptually separate from other components in a system for coordinating a radiological imaging subsystem with a component, for example.

A coordination device 340 may also be included in system 300, for example. A coordination device 340 may be integrated with other components of system 300 or may be separate, for example. The coordination device 340 may also provide mapping functionality (e.g. the coordination device 340 may include profile information corresponding to various components and radiological imaging subsystems), for example. As mentioned, profile information may also include profile information corresponding to a patient, for example. Using positional information of the various system components and subsystems, the coordination device 340 may be able to coordinate effective and/or efficient motions of the various components and subsystem, for example. The coordination device 340 may be able to, for example, coordinate a motion of a gantry on a radiological imaging subsystem such as to avoid collision with an imaging table. As another example, the coordination device 340 may be able to coordinate simultaneous motion between an automatically adjustable imaging table and a gantry on a radiological imaging subsystem.

System 300 may also include an image processing subsystem 350. The image processing subsystem 350 may be capable of receiving positional information (for example, from the mapping device 320 as shown in FIG. 3), for example. The positional information may be used in conjunction with image information received from the radiological imaging subsystem to generate radiological images, for example. For example, the position of a c-arm with respect to the imaging table may allow the image processing subsystem 350 to effectively display the orientation of a radiological image. As another example, angular information derived from the positional information may be incorporated in the radiological image through dimensional display and/or annotations.

FIG. 4 shows a flow chart 400 for a method for coordinating a radiological imaging subsystem with a component, according to an embodiment of the present invention. The steps of method 400 may be performed in an alternate order as shown, for example. At least some of the steps of method 400 may be performed simultaneously in part, for example. Furthermore, some steps of method 400 may be omitted (e.g. steps 410 and 412), for example. The steps of method may be performed by a computer and/or other processor executing a set of instructions on a computer-readable medium, for example.

At step 402 a first position may be determined based on a position of the radiological imaging subsystem. A first position may be determined, for example, by communicating with a first communication device (e.g. 104). Positional information may be dynamic (e.g. changeable). Alternatively, the position of the radiological imaging subsystem may be a reference position. For example, if the imaging subsystem is mobile, the position may be changeable. The position information may include coordinate information, orientation information, and/or profile information, for example. A plurality of communication devices on a radiological imaging subsystem may be employed to communicate various positional aspects of the imaging subsystem (e.g. position of the base, position of the gantry, etc.).

As discussed above, communications with the various communication devices may be active and/or passive, and may use a number of various communications media (e.g. optical, electromagnetic, sonic, etc.). Thus, the first position information may be actively transmitted by a first communication device, or may be inferred by the passive response from the first communication device (e.g. RFID), for example.

At step 404 a second position may be determined based on a position of a component. A second position may be determined, for example, by communicating with a second communication device (e.g. 108). Positional information may be dynamic (e.g. changeable). For example, if a component such as an imaging table is mobile, the position may be changeable. Alternatively, the position of the other component may be a reference position. The position information may include coordinate information, orientation information, and/or profile information, for example. A plurality of communication devices on the component may be employed to communicate various positional aspects of the imaging subsystem (e.g. position of the base, orientation of the table supporting the patient, etc.). It may also be possible to determine any number of positions of additional components by repeating step 404 for each successive component, for example.

As discussed above, communications with the various communication devices may be active and/or passive, and may use a number of various communications media (e.g. optical, electromagnetic, sonic, etc.). Thus, the second position information may be actively transmitted by a second communication device, or may be inferred by the passive response from the second communication device (e.g. RFID), for example.

At step 406 positional relationship between the radiological imaging subsystem and a component may be determined based at least in part on the first position and the second position. If positional information is available for additional components, the relationship among such additional components may also be determined. The positional relationship may include a coordinate relationship, orientation relationship, profile relationship, and/or the like, for example. The positional relationship may be determinable through a device, for example, such as a mapping device (e.g. 320). Alternatively, the positional relationship may be determinable in one or more of the communication devices (e.g. 104, 108, 110, 204, 208, or 330), for example. As discussed in steps 402 and 404, the positional information may include various aspects—coordinate, orientation, and/or profile, for example. Some of this information need not be part of the positional information, and may later be associated with the positional information, for example. As an example, the profiles of various subsystems and components may be stored in a device, such as a mapping device, which may receive the first and second positions, and then associate profile information to then obtain a positional relationship between the various subsystems and components, for example.

At step 408 a motion of the radiological imaging subsystem may be coordinated based at least in part on the positional relationship. Motion may be coordinated to avoid collision with a component or a patient, for example. Motion may include motion of the base, motion of the gantry, and/or motion of other aspects of a radiological imaging subsystem, for example. For example, the positional relationship may be used to coordinate the motion of a gantry about an imaging table in real-time.

At step 410 a motion of a component may be coordinated based at least in part on the positional relationship. For example, an imaging table may be moved and/or adjusted based on the position of the radiological imaging subsystem. Motion may be coordinated to avoid collision with the radiological imaging subsystem, a component, or a patient, for example. Motion may include motion of the base, motion of an imaging tabletop portion, and/or motion of other aspects of a component, for example. For example, the positional relationship may be used to coordinate movement of both a gantry and an imaging table, either simultaneously, or in alternation.

At step 412 an image may be processed based at least in part on the positional relationship. For example, an image processing subsystem (e.g. 350) may receive the positional information, and process a radiological image based on the positional relationship. For example, the position of a c-arm with respect to the imaging table may allow the for the processing of an image to effectively display the orientation of a radiological image. As another example, angular information derived from the positional information may be incorporated in the radiological image through dimensional display and/or annotations.

As an illustrative example, a method described in association with FIG. 4 may be performed in the following manner. At step 402, a first position is determined based on a position of the radiological imaging subsystem. In this example, the radiological imaging subsystem is mobile. The first position is determined by communicating with a device (e.g. 104, 204) located on the radiological imaging subsystem. The device is located on the base of the radiological imaging subsystem, and the first position information includes coordinate information and orientation information of the radiological imaging subsystem. A mapping device (e.g. 320) receives this information, and correlates profile information of the mobile radiological imaging subsystem in use. At step 404, a second position is determined based on a position of an imaging table. In this example, the imaging table is also mobile. The second position is determined by communicating with a second device (e.g. 108, 208) located on the imaging table. The device is located on the base of the imaging table, and the second position information includes coordinate information and orientation information of the imaging table. A mapping device (e.g. 340) receives this information, and correlates profile information of the mobile imaging table in use.

At step 406, a positional relationship between the mobile radiological imaging subsystem and the mobile imaging table is determined by the mapping device. The positional relationship includes coordinate information, orientation information, and profile information of both the radiological imaging subsystem and the imaging table. The positional information also incorporates feedback from a coordination device (e.g. 340) that is tracking any motion changes in both the radiological imaging subsystem and the imaging table. So, as the gantry moves, the coordination device tracks changes of the gantry position for use in determining a positional relationship. Additionally, if the position of the imaging table is automatically controllable, such changes in table position (e.g. angle, height, etc.) may also be tracked in real-time.

At step 408, a motion of the radiological imaging subsystem is coordinated based at least in part on the positional relationship. Based on the positional relationship determined by the mapping device, the coordination device calculates movement for effective radiological imaging without collision of various components, subsystems and/or patients. Similarly, at step 410, a motion of the imaging table is coordinated based at least in part on the positional relationship. Based on the positional relationship determined by the mapping device, the coordination device calculates movement for effective radiological imaging without collision of various components, subsystems and/or patients.

At step 412, an image is processed based at least in part on the positional relationship. The position of the c-arm during imaging with respect to the patient is used to effectively process a radiological image. The resulting radiological image contains angulation information helpful for clinical diagnosis of the patient.

In an embodiment, the various systems and methods described herein may incorporate one or more computer-readable media, such as a hard disk, floppy disk, CD, CD-ROM, DVD, compact storage, flash memory and/or other memory (such as memory 106). The medium may be in a communication device (e.g. 104, 108, 110, 204, 208, or 330), a mapping device (e.g. 320), a coordination device (e.g. 340) and/or in a separate portion of a system. More than one media may be distributed among various system elements described herein. The medium may include a set of instructions capable of execution by a computer or other processor. The communication, position determination, and motion coordination functions described above may be implemented as instructions on the computer-readable medium. For example, the set of instructions may include a determination routine that determines a first position based on a position of a radiological imaging subsystem. Additionally, the set of instructions may include a determination routine that determines a second position based on a position of a component. Additionally, the set of instructions may include a determination routine to determine a positional relationship between the radiological imaging subsystem and a component based at least on the first and second positions. Additionally, the set of instructions may include a coordination routine for coordinating a motion of the radiological imaging subsystem based at least in part on the positional relationship. In an embodiment, the set of instructions may include a coordination routine for coordinating a motion of the other component based at least in part of the positional relationship. In an embodiment, the set of instructions may include a processing routine for processing an image based at least in part of the positional relationship.

Thus, embodiments of the present application provide radiological imaging subsystems capable of performing advanced gantry functions and collision avoidance from a recognized spatial relationship between the imaging subsystem and a component, such as an imaging table, or a patient located thereon. Embodiments of the present application provide radiological imaging systems for coordinated motion between an imaging table and a radiological imaging subsystem. Additionally, embodiments of the present application provide radiological imaging methods and systems that can ascertain the position and/or orientation of other components.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. For example, features may be implemented with software, hardware, or a mix thereof. Therefore, it is intended that the invention not be limited to the particular embodiment disclosed, but that the invention will include all embodiments falling within the scope of the appended claims.

The invention claimed is:

1. A system for coordinating a radiological imaging subsystem with an imaging table, the system comprising:
   a first communication device located on the radiological imaging subsystem, the radiological imaging subsystem comprising a gantry; and
   a second communication device located on the imaging table,
   wherein said first communication device and said second communication device are capable of communicating to indicate a positional relationship between the radiological imaging subsystem and the imaging table.

2. The system of claim 1, wherein at least one range of motion of the radiological imaging system is determinable based at least in part on said positional relationship.

3. The system of claim 2, wherein said at least one range of motion of the radiological imaging subsystem comprises at least one range of motion of said gantry.

4. The system of claim 1, wherein said first communication device and said second communication device are capable of communicating in a medium comprising at least one of an active radio frequency medium, an active optical medium, an active sonic medium, a passive radio frequency medium, or a passive optical medium.

5. The system of claim 1, wherein said first communication device and said second communication device are capable of communicating with each other.

6. The system of claim 1, wherein said first communication device and said second communication device are capable of communicating with a third device.

7. The system of claim 1, wherein the radiological imaging subsystem is substantially mobile.

8. The system of claim 1 further comprising an image processing subsystem capable of receiving said positional relationship for processing radiological image information generated by at least one of the radiological imaging subsystem or the imaging table.

9. A method for coordinating a radiological imaging subsystem and an imaging table, the method comprising:
   determining a first position based on a position of the radiological imaging subsystem, the radiological imaging subsystem capable of being substantially mobile and comprising a gantry;
   determining a second position based on a position of the imaging table;
   determining a positional relationship between the radiological imaging subsystem and the imaging table based at least in part on said first position and said second position;
   communicating with a first device located on the radiological imaging subsystem and a second device located on the imaging table to determine said first position and said second position; and coordinating a motion of the radiological imaging subsystem based at least in part on said positional relationship.

10. The method of claim 9, further comprising coordinating a motion of the imaging table based on said positional relationship.

11. The method of claim 10, wherein said motion of the radiological imaging subsystem comprises a motion of said gantry.

12. The method of claim 9 further comprising processing an image based at least in part on said positional relationship.

13. A computer-readable storage medium including a set of instructions for a computer, the set of instructions comprising:
 a reception routine to receive positional information provided by a first communication device located on a radiological imaging subsystem, said radiological imaging subsystem comprising a gantry and provided by a second communication device located on an imaging table;
 a determination routine to determine a positional relationship between said radiological imaging subsystem and said imaging table, said positional relationship based at least in part on said positional information; and
 a coordination routine to coordinate a motion of said radiological imaging subsystem with respect to a position of said imaging table.

14. The set of instructions of claim 13 further comprising a coordination routine to coordinate a motion of said imaging table with respect to a position of said radiological imaging subsystem.

15. The set of instructions of claim 13, wherein said first communication device and said second communication device are capable of communicating with each other.

16. The set of instructions of claim 13 further comprising an image processing routine capable of receiving said positional information to process image information from said radiological imaging subsystem.

17. A system for coordinating a radiological imaging subsystem with an imaging table, the system comprising:
 a first communication device located on the radiological imaging subsystem, the radiological imaging subsystem comprising a gantry, said first communication device capable of communicating information corresponding to a position of the radiological imaging subsystem;
 a second communication device located on the imaging table, said second communication device capable of communicating information corresponding to a position of the imaging table; and
 a mapping device capable of receiving said information corresponding to said position of the radiological imaging subsystem and said position of the imaging table to determine a spatial relationship between the radiological imaging subsystem and the imaging table.

18. The system of claim 17 further comprising a coordination device configured to record a motion of the radiological imaging subsystem with respect to the imaging table based at least in part on said spatial relationship.

19. The system of claim 17 further comprising a coordination device for coordinating a motion of the imaging table with respect to the radiological imaging subsystem based at least in part on said spatial relationship.

20. The system of claim 17, wherein the radiological imaging subsystem is substantially mobile.

21. The system of claim 17, wherein the first communication device and said second communication device are capable of communicating with each other.

22. The system of claim 17 further comprising an image processing subsystem capable of receiving said spatial relationship for processing image information from said radiological imaging subsystem.

23. A method for coordinating a radiological imaging subsystem with an imaging table, the method comprising:
 receiving positional information provided by a first communication device located on a radiological imaging subsystem, said radiological imaging subsystem comprising a gantry, and provided by a second communication device located on the imaging table;
 determining a positional relationship between the radiological imaging subsystem and the imaging table, said positional relationship based at least in part on said positional information;
 and coordinating a motion of the radiological imaging subsystem with respect to a position of the imaging table.

24. The method of claim 23 further comprising coordinating a motion of the imaging table with respect to a position of the radiological imaging subsystem.

25. The method of claim 23, wherein said first communication device and second communication device are capable of communicating with each other.

26. The method of claim 23 further comprising receiving said positional information to process image information from said radiological imaging subsystem.

* * * * *